United States Patent
Hatto (10) Patent No.: US 11,944,561 B2
(45) Date of Patent: Apr. 2, 2024

(54) TOE WALKING PREVENTION ARTICLE

(71) Applicant: BraceAbility, Inc., Cedar Falls, IA (US)

(72) Inventor: Melanie Deborah Hatto, Cape Coral, FL (US)

(73) Assignee: BraceAbility, Inc., Cedar Falls, IA (US)

( * ) Notice: Subject to any disclaimer, the term of this patent is extended or adjusted under 35 U.S.C. 154(b) by 0 days.

(21) Appl. No.: 17/104,551

(22) Filed: Nov. 25, 2020

(65) Prior Publication Data
US 2022/0160530 A1    May 26, 2022

(51) Int. Cl.
    *A61F 5/01* (2006.01)

(52) U.S. Cl.
    CPC .................................. *A61F 5/0111* (2013.01)

(58) Field of Classification Search
    CPC ........ A61F 5/01; A61F 5/0102; A61F 5/0104; A61F 5/0111; A61F 5/0113; A61F 5/0127; A61F 5/019; A61F 5/0195; A61F 5/058; A61F 5/0582; A61F 5/05825; A61F 5/05841; A61F 5/0585; A61F 13/06; A61F 13/064; A61F 13/065; A61F 13/067; A61F 5/32; A61F 13/066; A61F 13/104; A61F 13/068; A43B 13/28; A43B 7/1445; A41B 1100/004; A41B 1100/005; A41B 1100/08
    See application file for complete search history.

(56) References Cited

U.S. PATENT DOCUMENTS

| 4,351,324 | A | | 9/1982 | Bronkhorst | |
|---|---|---|---|---|---|
| 5,925,010 | A | * | 7/1999 | Caprio, Jr. | A61F 13/107 602/62 |
| 2006/0276737 | A1 | * | 12/2006 | Rose | A61F 5/019 128/893 |
| 2009/0044424 | A1 | * | 2/2009 | Kohler | A43B 7/1445 36/43 |
| 2013/0204172 | A1 | * | 8/2013 | Viehweg | A61F 13/066 602/26 |
| 2018/0028116 | A1 | * | 2/2018 | Fulton | A61F 5/32 |

OTHER PUBLICATIONS

Memsnet Material: Copper (Cu) Bulk, 2021, [online] Retreived on Sep. 27, 2021 from https://www.memsnet.org/material/coppercubulk/ (Year: 2021).*

* cited by examiner

*Primary Examiner* — Ophelia A Hawthorne
*Assistant Examiner* — Gina McCarthy
(74) *Attorney, Agent, or Firm* — Bochner PLLC; Andrew D. Bochner (57) ABSTRACT

A toe walking prevention article includes a first component being a soft material or a flexible material having a length in a length direction at least extending from a middle of a foot of a wearer to toes of the foot. The first component has at least one securing feature configured to be secured to the foot. A rigid component being a stiff material is securely attached to the first component configured for placement underneath the ball. When the wearer toe walks so that the heel is off a ground, the rigid component pushes on a sensory nerve located at the ball of the foot which causes an uncomfortable sensation to the wearer. Responsive to the uncomfortable sensation, the wearer moves the heel of the foot onto the ground.

19 Claims, 7 Drawing Sheets

TOE WALKING PREVENTION ARTICLE

FIELD

This Disclosure relates to therapeutic walking articles for individuals that may have a tendency to walk, run, or stand, on the ball(s) of their feet/foot or on their toes.

BACKGROUND

Toe walking braces are worn to help prevent tip toe walking (hereafter toe walking), or a gait movement pattern, where the individual walks, runs, or stands on the ball of their feet or on their toes. Toe walking is most commonly a condition in young children and is often idiopathic in nature (unknown reasons). Toe walking begun in one's childhood can also be continued into adulthood. If toe walking is left untreated, toe walking can cause severe muscle tightness of the calf muscles, and can even result in damaging the bone structure in the foot.

Regarding the anatomy of the feet, the feet are known to be flexible structures comprising bones, joints, muscles, and soft tissues that allow individuals to stand upright and perform activities including standing, walking, running, and jumping. The feet are conventionally divided into three sections based on their position in the length dimension of the foot. The forefoot contains the five toes (phalanges) and the five longer bones (metatarsals). The midfoot is a pyramid-like collection of bones that form the arch of the foot. These bones include the three cuneiform bones, the cuboid bone, and the navicular bone. The hindfoot forms the heel and ankle. The talus bone supports the leg bones (tibia and fibula), forming the ankle. The calcaneus (heel bone) is the largest bone in the foot.

Muscles, tendons, and ligaments run along the surfaces of the feet, allowing the complex movements needed for motion and balance. The Achilles tendon connects the heel to the calf muscle, and is recognized as being essential for running, jumping, and standing on the toes.

The lower leg is located below the knee and is commonly referred to as the calf. The two major calf muscles are the gastrocnemius muscle and the soleus muscle. Both of these calf muscles merge at the base of the calf, where they transition into becoming the Achilles tendon, which attaches to the bottom of the foot. The calf muscles and Achilles tendons work together to help individuals lift their heels when they walk.

A conventional toe walking brace functions by limiting or preventing plantar flexion of the ankle, where plantar flexion refers to the movement of the foot when the foot is bent at the ankle away from the body. This plantar flexion limiting function is most commonly accomplished by reducing ankle mobility using a stiff (or rigid) plastic 'foot', ankle-foot orthosis (AFO), a fiberglass casting over the lower leg and foot, or a tape. Physical and occupational therapy treatment for toe walking conventionally includes muscle lengthening, gait training, toe taping, and desensitizing training.

SUMMARY

This Summary is provided to introduce a brief selection of disclosed aspects in a simplified form that are further described below in the Detailed Description including the drawings provided. This Summary is not intended to limit the claimed subject matter's scope.

The problem of toe walking is solved by disclosed toe walking prevention articles, such as a toe walking prevention brace, sock, or sleeve, that include what is termed herein as a "rigid component". A rigid component as used herein refers to a relatively stiff component of the toe walking prevention article that is securely attached to a flexible middle structure in the case of a disclosed toe walking prevention brace, or a soft material in the case of a disclosed toe walking prevention sock or a toe walking prevention sleeve. The rigid component is configured when the toe walking prevention article is worn by the wearer to be positioned over the ball of the foot.

In response to the wearer of the toe walking prevention article beginning to toe walk, the rigid component applies pressure on the sensory nerves in the epidermis in the ball of the foot, which creates an uncomfortable/negative sensation to the wearer. This uncomfortable sensation prompts the wearer when toe walking to promptly move the position of his or her foot by placing their heel on the ground to change from utilizing a toe walking gait pattern with a forefoot strike where the ball of foot lands first to begin utilizing a normal heel to floor gait pattern. The normal heel to toe gait pattern can be either a midfoot strike where the heel and the ball land simultaneously, or a heel strike where the heel of foot lands, then plantar flexes to the ball.

Disclosed toe walking prevention articles are adjustable with respect to the positioning of the rigid component. By slightly rotating the toe walking prevention article to the right or to the left, the position of the rigid component changes. This can be done for the reason that different wearers may toe walk more on the outside of their foot or more on the inside of their foot. Disclosed toe walking prevention articles are also generally comfortable to wear as long as the wearer is utilizing a normal heel to toe gait pattern so that the toe wearer generally forgets they are wearing the toe walking prevention article provided the wearer is not currently toe walking.

Disclosed aspects include a toe walking prevention article comprising a first component comprising a soft material or a flexible material having a length in a length direction at least extending from a middle of a foot of a wearer to the toes of the foot. The first component has at least one securing feature configured to be secured to the foot. For a disclosed sock or a disclosed sleeve, the securing feature is the elasticity of the soft material, while for the brace the securing feature is top straps and bottom straps. As described above the rigid component is a stiff material that is securely attached, such as bonded such as laminated, glued, or sewn, to the first component, where the toe walking prevention article is configured for placement of the rigid component underneath the ball of the foot.

The rigid component can be located and secured on the inside or on the outside of the first component. Disclosed toe walking prevention articles are distinct as compared to known therapeutic walking articles typically being walking braces, which as described above comprise a rigid or stiff material throughout, such as a hard plastic material, by instead having the middle structure comprised of a flexible material (in the case of a brace) or a soft material (in the case of a sock or a sleeve).

DETAILED DESCRIPTION

Disclosed aspects are described with reference to the attached figures, wherein like reference numerals are used throughout the figures to designate similar or equivalent elements. The figures are not drawn to scale and they are provided merely to illustrate certain disclosed aspects. Several disclosed aspects are described below with reference to example applications for illustration. It should be understood that numerous specific details, relationships, and methods are set forth to provide a full understanding of the disclosed aspects.

Figure 1A:
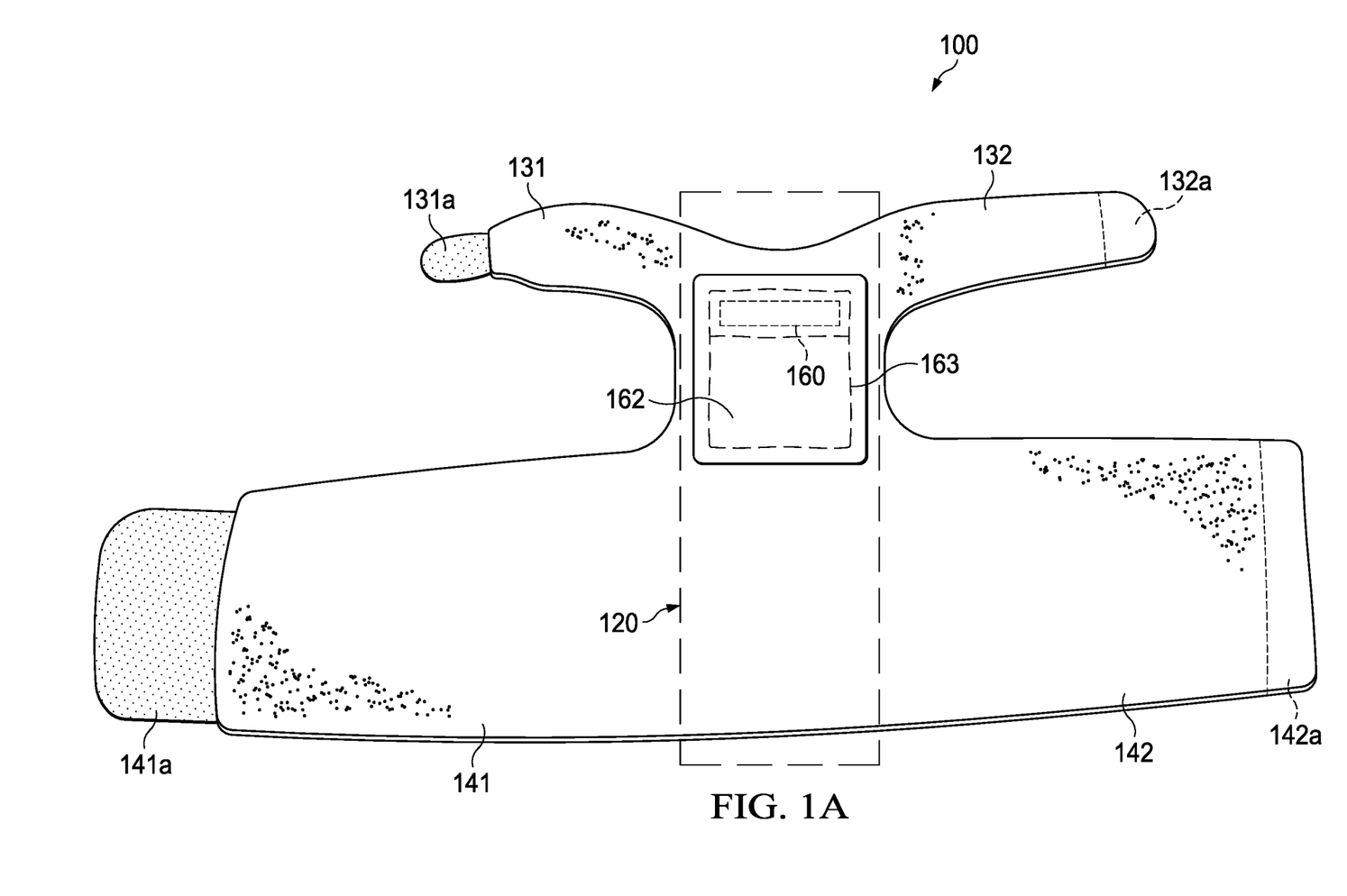
FIG. 1A is a top view depiction of a disclosed toe walking prevention brace showing its inside surface on top including a rigid component that is configured so that when the toe walking prevention brace is worn by a wearer the rigid component is in contact with the ball of the foot of the wearer, according to an example aspect.

FIG. 1A is a top view depiction of a disclosed toe walking prevention brace 100 showing its inside surface on top including a rigid component 160 which is fixed in place that is configured so that when the toe walking prevention brace 100 is worn by a wearer the rigid component 160 is in contact with a ball of the foot, according to an example aspect. The rigid component 160 comprises a stiff material that has a Young's modulus at room temperature of at least 3 GPa, such as having Young's modulus of 3 GPa to 50 GPa. In one example, the rigid component 160 can comprise polycarbonate known to be a relatively strong plastic that has a Young's modulus of 13 to 21 GPa, acrylic that has Young's modulus of 3 GPa, or polyether ether ketone (PEEK) that has a Young's modulus of 3.6 GPa. The rigid component 160 can also comprise non-polymer materials such as a metal or a metal alloy, as well as a ceramic, or a glass, where non-polymer materials can provide a room temperature Young's modulus generally from 3 GPa to several hundred GPa.

The toe walking prevention brace 100 comprises a first component 120 shown as a middle structure comprising a flexible material having a length that is sufficient for extending from a middle of a foot of a wearer to the toes of the foot. The same flexible material utilized by the first component 120 when it comprises a middle structure can extend beyond the middle structure in an integrated (one piece) arrangement to also provide the top straps 131, 132 and the bottom straps 141, 142. A thickness of the flexible material is generally 1 mm to 6 mm.

The ball of the foot is known to be the padded portion of the sole of the human foot between the toes and the arch, that includes a sensory nerve, on which the weight of the body rests when the heel is raised. The ball of the foot is named for the largest metatarsal bone that is shaped like a ball.

A flexible material (e.g. a rubber) as known in physics and material science has a relatively low room temperature Young's modulus, and the flexible material changes its shape considerably under a load. The flexible material can comprise an elastomeric material to provide significant flexibility including stretchability. The term "integrated" in this context means one single piece of flexible material, so that there is no adhesive or other material interfaces between the first component 120 and the straps 131, 132, 141, 142.

The flexible material of the first component 120 can also comprise a non-elastomeric material, or a mixture of an elastomeric material and a non-elastomeric material. As used herein a "flexible material" refers to a material that has a Young's modulus at room temperature of less than 0.5 GPa. It is noted that rubber is known to have Young's modulus at room temperature of <0.01 to about 0.1. One example flexible material that can be used is neoprene (also called polychloroprene), which is known to be a family of synthetic rubbers produced by polymerization of chloroprene, where neoprene is known to exhibit good chemical stability and maintains flexibility over a wide temperature range including room temperature. The flexible material may also comprise a flexible foam, such as neoprene foam, polyurethane foam, or another elastomer-based flexible polymer foam.

The first component 120 when comprising a middle structure on its inside surface may optionally be lined with a layer of soft material such as nylon, polyester, satin, or cotton. The layer of soft material may be sown to be encased in a sleeve, or attached by an adhesive to the first component 120.

The first component 120 because it comprises a flexible material does not restrict plantar flexion. However, having a disclosed rigid component 160 also included with the toe walking prevention brace 100 creates an uncomfortable sensation to the wearer when the wearer toe walks which places a portion of their body weight onto the ball of their foot, and thus to the rigid component 160. The toe walking prevention brace 100 can be worn with or without shoes or other footwear, with a separate toe walking prevention brace 100 for each of the feet, although the toe walking prevention brace can be worn on only one of the feet of the wearer. The toe walking prevention brace 100 can also assist with maintaining (a neutral) foot pronation, where pronation refers to a natural movement of the foot that occurs during foot landing while running or while walking.

The top straps 131, 132 and bottom straps 141, 142 on respective ends of the first component 120 can be seen to branch off the first component 120. The top straps 131, 132 and the bottom straps 141, 142 each have at least one inter-strap fastener having respective fastening features located on their distal ends shown in FIG. 1A comprising a first attachment end 131a, 141a and an oppositely located second attachment end 132a, 142a. The first attachment ends 131a, 141a and the second attachment ends 132a, 142a can comprise hooks on one attachment and loops on the other attachment end, such as a VELCRO or a similar arrangement. For example, in the case of a VELCRO arrangement, one attachment end can comprise an Un-Broken Loop fabric (UBL) has that is hook compatible. UBL can provide high stretch and hook compatible durability.

The bottom straps 141, 142 are configured to wrap around the arch of the foot. The arch of the foot is known to be located near the middle of the foot in the length direction of the foot. The bottom straps 141, 142 are generally greater in length and width, as compared to the top straps 131, 132. The top straps wrap 131, 132 are configured to wrap around at least one toe of the wearer shown, for example, in FIG. 2A described below as being wrapped around the second, third, and fourth of the toes. The top straps 131, 132 and bottom straps 141, 142 are shown oriented parallel to one another.

The rigid component 160 that as described above comprises a hard material can be optionally encased within an outer layer 162 which is softer as compared to the rigid component 160. A sewn pattern 163 as shown in FIG. 1A is for attaching the rigid component 160 and the outer layer 162 to the first component 120. Alternatively, the rigid component 160 can be otherwise attached to the first component 120, such as being directly attached by being glued by an adhesive to the first component 120 so that there would be no need for an outer layer 162 or the sewn pattern 163.

The rigid component 160 is thus secured on the top inside surface of the first component 120 as shown in FIG. 1A, so that when the wearer is toe walking and the ball of the foot of the wearer comes in contact with the rigid component 160, the rigid component 160 puts pressure on the sensory nerves located in the ball of the foot. By pressing on the sensory nerves in the ball of the foot serves to alert the wearer when toe walking occurs by inducing an uncomfortable feeling to prompt the wearer to stop toe walking by beginning to place their heel onto the ground while walking.

Besides being sewn or glued, the outer layer 162 when included may also be attached to the first component 120 using a variety of other attachment arrangements, such as being laminated horizontally to the top portion of the inside surface of the first component 120. The rigid component 160 is shown by example being rectangularly shaped, and running parallel in its length direction relative to the length direction of the top straps 131, 132, and the bottom straps 141, 142.

The top straps 131, 132 after their first attachment end 131a and the second attachment end 132a, respectively, are attached together, hold the rigid component 160 in place underneath the ball of the foot of the wearer. The bottom straps 141, 142 after their first attachment end 141a and the second attachment end 142a are attached together hold the first component 120 in place under the arch of the foot of the wearer.

Figure 1B:
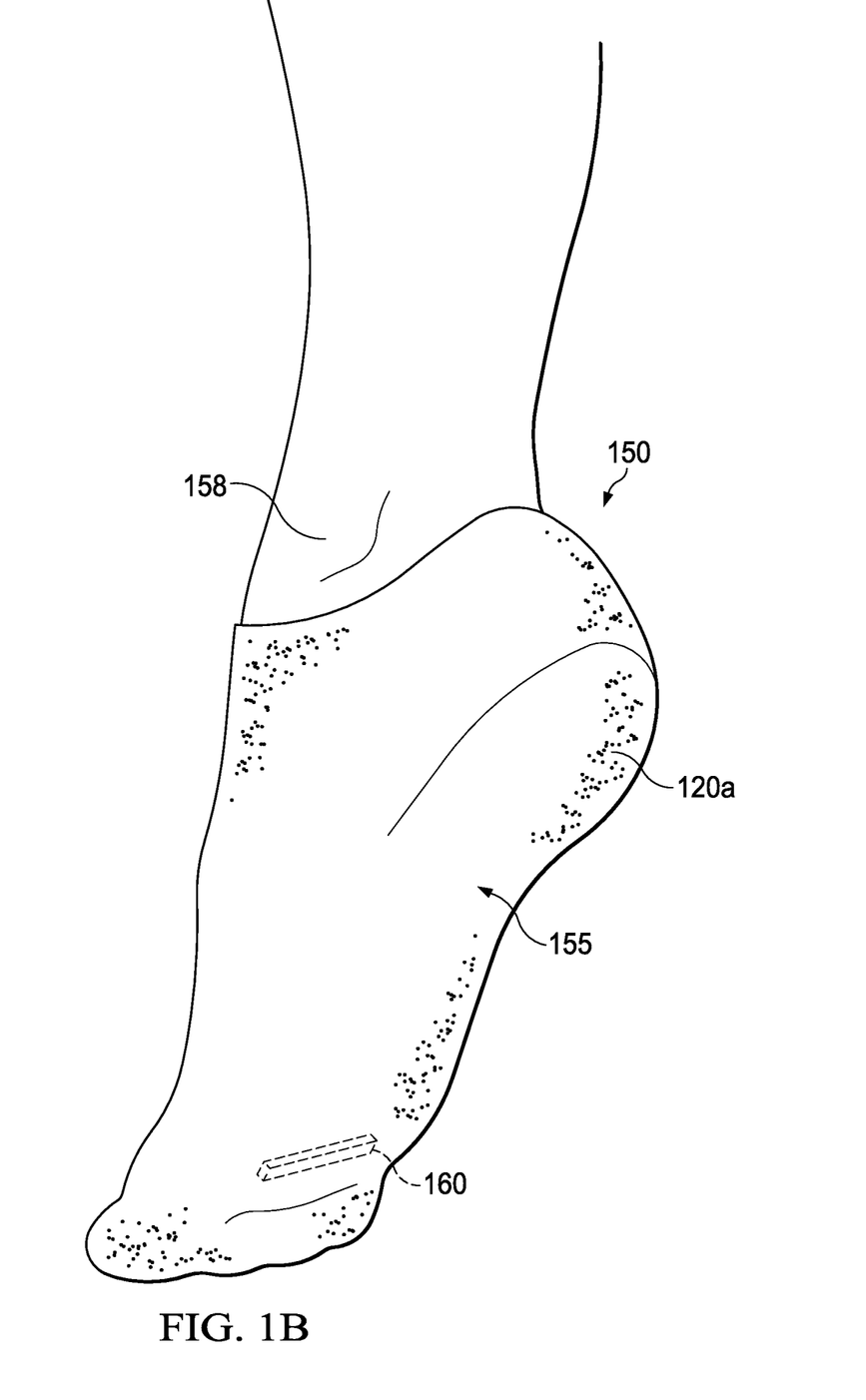
FIG. 1B depicts the toe walking prevention article as a toe walking prevention sock including a rigid component that is configured so that when the toe walking prevention sock is worn by a wearer the rigid component is in contact with the ball of the foot, according to an example aspect.

FIG. 1B depicts the toe walking prevention article as a toe walking prevention sock 150 including a rigid component 160 that is configured so that when the toe walking prevention sock is worn by a wearer the rigid component 160 is in contact with the ball of the foot of the wearer, according to an example aspect. For a disclosed toe walking prevention sock 150 or sleeve described below relative to FIGS. 1C and 1D, such as the toe walking prevention sock 150, the first component when it comprises a soft material (soft material) 120a configured in an elliptical cross-sectional area. For the toe walking prevention sock 150, as with the conventional sock, the securing feature is provided by an elasticity of the soft material, and a length of the toe walking prevention sock 150 in the length direction extends at least from an ankle 158 of the wearer to the toes of the wearer. As with the above-described toe walking prevention brace 100, the rigid component 160 can be attached by a variety of methods, such as being sewn or glued, on the inside surface or the outside surface of the soft material 120a to be secured on the bottom of the foot 155 of the wearer in the area over the ball of the foot.

Figure 1C:
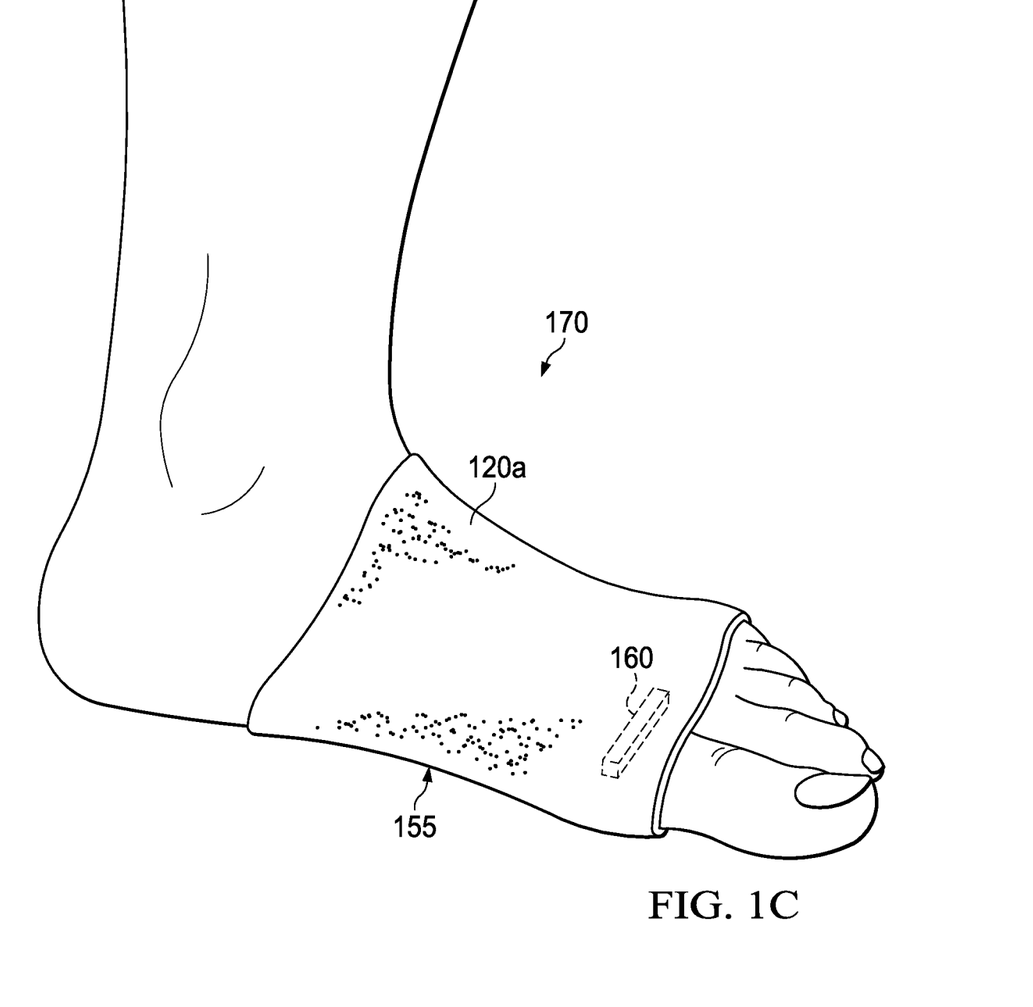
FIG. 1C depicts the toe walking prevention article as a toe walking prevention sleeve that does not cover the toes including a rigid component that is configured so that when the toe walking prevention sleeve is worn by a wearer the rigid component is in contact with the ball of the foot, according to an example aspect.

FIG. 1C depicts the toe walking prevention article as a toe walking prevention sleeve 170 comprising a soft material 120a that does not cover the toes including a rigid component 160, according to an example aspect. The toe walking prevention sleeve 170 is configured so that when the toe walking prevention sleeve 170 is worn by a wearer the rigid component 160 is in contact with the ball of the foot of the wearer.

Figure 1D:
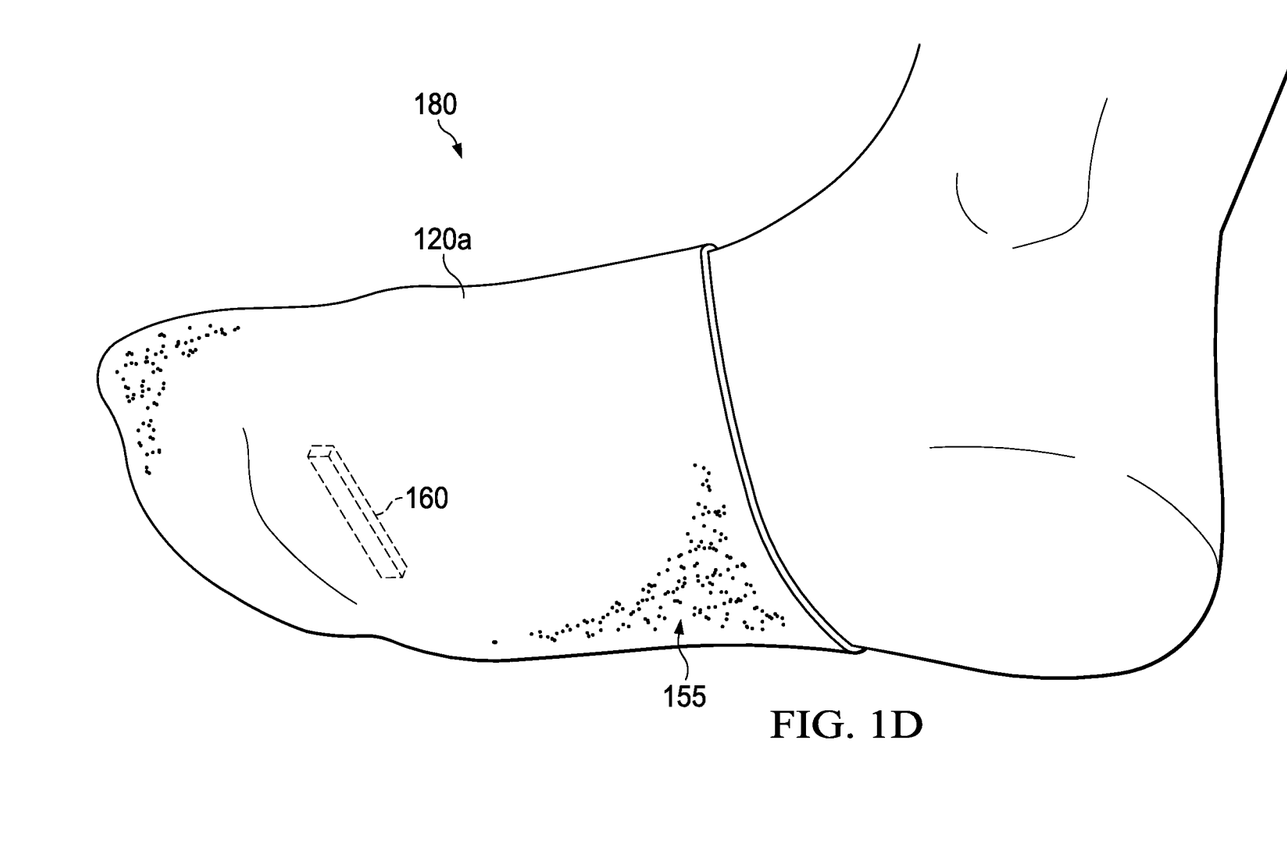
FIG. 1D depicts the toe walking prevention article as a toe walking prevention sleeve that extends to cover the toes, including a rigid component that is configured so that when the toe walking prevention sleeve is worn by a wearer the rigid component is in contact with the ball of the foot of the wearer, according to an example aspect.

FIG. 1D depicts the toe walking prevention article as a toe walking prevention sleeve 180 comprising a soft material 120a, according to an example aspect. The toe walking prevention sleeve 180 extends to cover the toes and includes a rigid component 160 that is configured so that when the toe walking prevention sleeve 170 is worn by a wearer the rigid component 160 is in contact with the ball of the foot of the wearer.

Figure 2A:
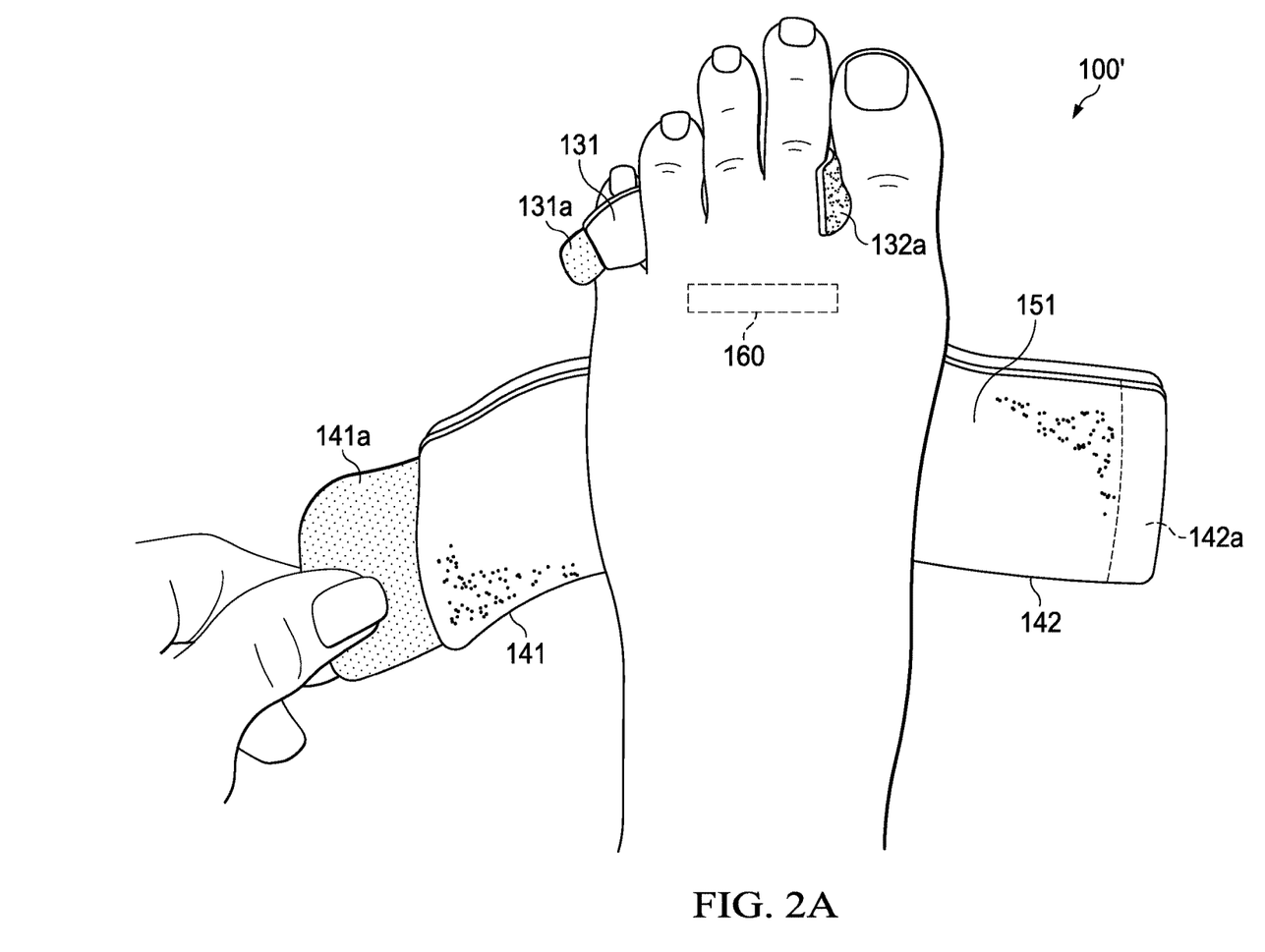
FIG. 2A is a front view depiction of a wearer holding a disclosed toe walking prevention brace before the wearer completes wrapping of the straps around their toes and arch to secure the toe walking prevention brace, showing one side (such as the hook side or the loop side) of the fastening mechanism, according to an example aspect.

FIG. 2A is a front view depiction of a wearer holding a disclosed toe walking prevention brace now shown as 100' before the wearer completes wrapping of the top straps 131, 132 and bottom straps 141, 142 around their toes and arch, respectively, and then attaching the attachment ends 131a to 132a and 141a to 142a, showing one side (such as the hook side or loop side) of the fastening mechanism, according to an example aspect. The toe walking prevention brace 100' is shown including a liner 151 (which is optional) on at least an inside surface of the middle structure, shown in FIG. 2A also extending onto the inside surface of the bottom straps 141, 142.

The middle structure which also has the liner 151 thereon cannot be seen in FIG. 2A due to the presence of the wearer's foot on the middle structure. The liner 151 generally comprises a soft fabric that can be selected from nylon, polyester, satin, and cotton. Although the rigid component 160 is also not visible in FIG. 2A due to the presence of the wearer's foot on the middle structure, the rigid component 160 is shown in phantom. One of the top straps shown as 131 having an attachment end 131a is shown between the first and second toe, and the attachment end of the other top strap shown as 132a is shown between the fourth and the fifth toe (the big toe).

Figure 2B:
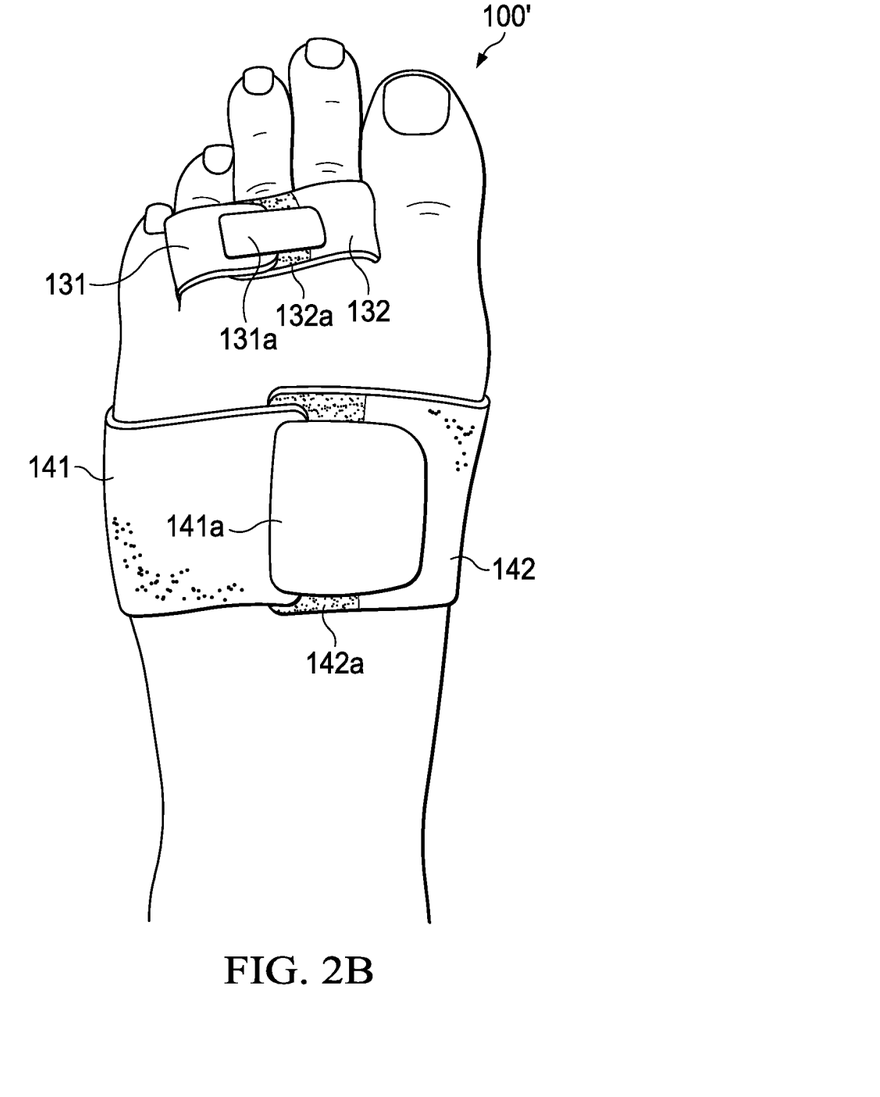
FIG. 2B is a front view depiction of a wearer having a disclosed toe walking prevention brace with the top straps positioned around the wearer's second, third, and fourth toes, and the bottom straps which may be referred to as arch straps positioned around the arch of the wearer's foot, according to an example aspect.

FIG. 2B is a front view depiction of a wearer having a disclosed toe walking prevention brace 100' with the top straps 131, 132 positioned and secured by attachment end 131a shown attached to attachment end 132a shown around the wearer's second, third, and fourth toes. The bottom straps 141, 142 which may be referred to as arch straps are positioned and secured by attachment end 141a which is attached to the other attachment end 142a around the arch of the wearer's foot.

Figure 3:
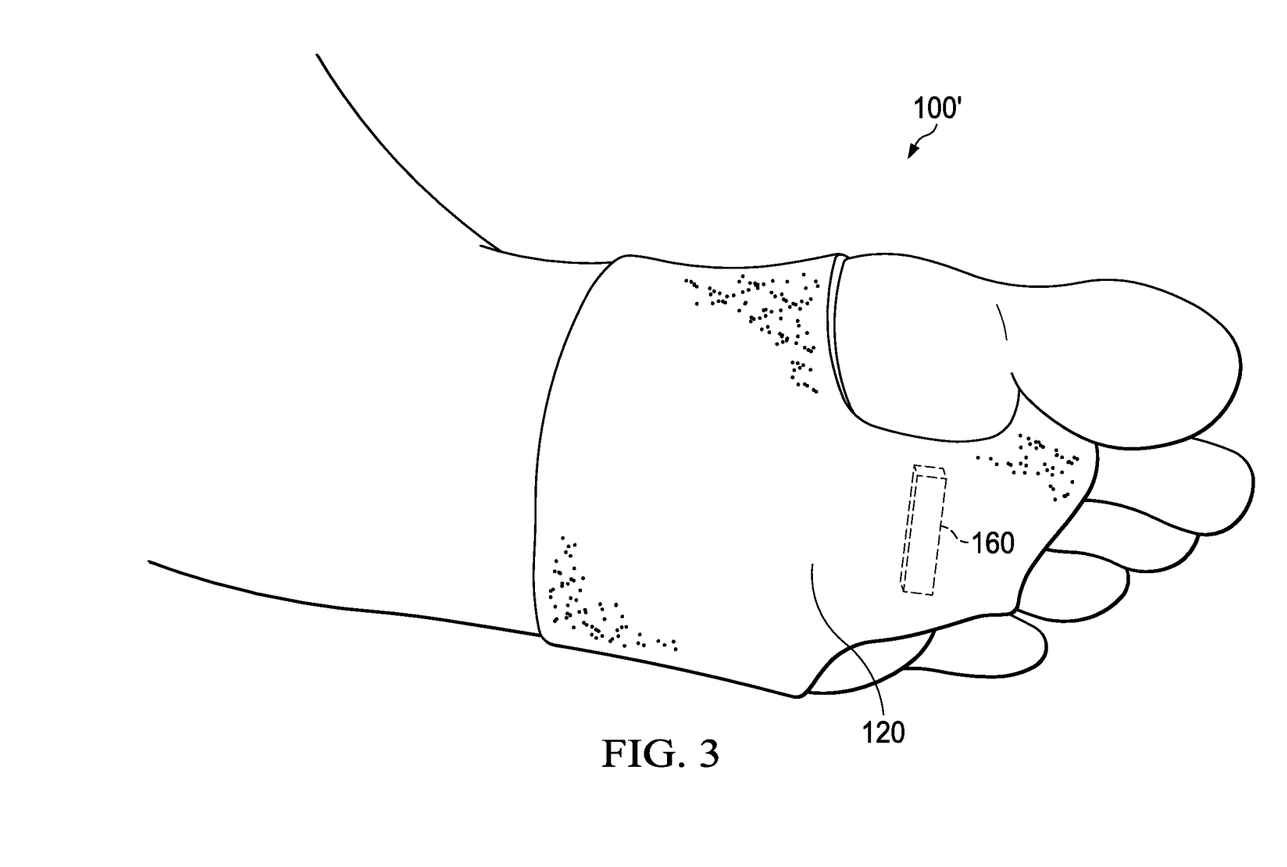
FIG. 3 is a plantar view depiction of the bottom side of a wearer having a disclosed toe walking prevention brace positioned around his or her foot and toes, according to an example aspect.

FIG. 3 is a plantar view depiction of the bottom side of a wearer having a disclosed toe walking prevention brace 100' positioned around his or her foot and toes. With the top straps 131, 132 and the bottom straps 141, 142 secured by their attachment ends, as described above, the rigid component 160 is shown in phantom because it would not be otherwise visible from the bottom side view being positioned under the ball of the wearer's foot.

Disclosed toe walking prevention articles thus allow a wearer when walking or running to maintain a normal heel to toe gait pattern. As described above, when a wearer of a disclosed toe walking prevention article attempts toe walking by lifting their heels off the ground so that their weight is placed on the ball of their feet or on their toes, the rigid component 160 creates a negative sensation/discomfort by pressing on the sensory nerve in the ball of the wearer's foot. This negative sensation/discomfort promptly encourages the wearer when walking or running to bring their heel back on to the ground to begin utilizing a normal heel to toe gait pattern.

While various disclosed aspects have been described above, it should be understood that they have been presented by way of example only, and not limitation. Numerous changes to the subject matter disclosed herein can be made in accordance with this Disclosure without departing from the spirit or scope of this Disclosure. In addition, while a particular feature may have been disclosed with respect to only one of several implementations, such feature may be combined with one or more other features of the other implementations as may be desired and advantageous for any given or particular application.

The invention claimed is:

1. A toe walking prevention article, comprising:
   a first component comprising a soft material or a flexible material having a length in a length direction configured for at least extending from a middle of a foot of a wearer to toes of the foot;
   wherein the first component has at least one securing feature configured to be secured to the foot;
   a rigid component comprising a stiff material securely attached to the first component via an outer layer encasing the rigid component, and configured for placement underneath a ball of the foot,
   wherein at least a perimeter of the outer layer is permanently attached to the first
   component, and wherein a surface area of the outer layer is less than a surface area
   of the first component;
   wherein the first component or the securing feature is configured for being positioned between the rigid component and the foot, and wherein the rigid component is disposed onto an outside surface of the first component or the securing feature.

2. The toe walking prevention article of claim 1, wherein the toe walking prevention article comprises a toe walking prevention brace, the toe walking prevention brace comprising:
   the first component being a middle structure comprising the flexible material;
   wherein the securing feature comprises top straps and bottom straps on respective ends of the middle structure branching off and being integrated with the middle structure, wherein the top straps and the bottom straps each having a first attachment end and oppositely located second attachment end configured to attach to the first attachment end, wherein the bottom straps are configured to wrap around an arch of the foot, and wherein the top straps are configured to wrap around at least one of the toes;
   wherein the rigid component is attached to the middle structure configured for placement underneath the ball,
   wherein the first attachment end and the second attachment end of the top straps after being attached are configured to hold the middle structure and the rigid component in place underneath the ball, and
   wherein the first attachment end and the second attachment end of the bottom straps after being attached are configured to hold the middle structure in place under the arch.

3. The toe walking prevention article of claim 2, wherein the first attachment end and the second attachment end of the top straps and the bottom straps both collectively comprise hooks and loops.

4. The toe walking prevention article of claim 2, wherein the middle structure comprises an elastomeric foam, and wherein a thickness of the elastomeric foam is between 1 mm and 6 mm.

5. The toe walking prevention article of claim 2, wherein an inside surface of at least the middle structure is lined with a soft fabric selected from nylon, polyester, satin, and cotton.

6. The toe walking prevention article of claim 1, wherein the toe walking prevention article comprises a toe walking prevention sock, the toe walking prevention sock comprising:
   the first component being a soft material configured in an elliptical cross-sectional area,
   wherein the length in the length direction is configured for extending at least from an ankle of the wearer to the toes, and wherein the securing feature is provided by an elasticity of the soft material.

7. The toe walking prevention article of claim 1, wherein the toe walking prevention article comprises a toe walking prevention sleeve, the toe walking prevention sleeve comprising:
   the first component being a soft material configured in an elliptical cross-sectional area,
   wherein the length in the length direction is configured for extending from at least the middle of the foot but not reaching an ankle to the toes, and wherein the securing feature is provided by an elasticity of the soft material.

8. The toe walking prevention article of claim 1, wherein the rigid component consists of a single structure.

9. The toe walking prevention article of claim 1, wherein the rigid component is glued by an adhesive to the first component.

10. The toe walking prevention article of claim 1, wherein the stiff material provides a Young's modulus at room temperature of at least 10 GPa.

11. A method of preventing toe walking, comprising:
   providing a toe walking prevention article including a first component comprising a soft or flexible material having a length and a length direction configured for at least extending from a middle of a foot of a wearer to toes of the foot, the foot including a heel, an arch, and a ball located below the toes, wherein the first component has at least one securing feature configured to secure to the foot; including a rigid component comprising a stiff material securely attached to the first component via an outer layer encasing the rigid component, and configured for placement underneath the ball, wherein at least a perimeter of the outer layer is permanently attached to the first component, wherein a surface area of the outer layer is less than a surface area of the first component, wherein the first component or the securing feature is configured for being positioned between the rigid component and the foot, and wherein the rigid component is disposed onto an outside surface of the first component or the securing feature;
   attaching the toe walking prevention article to the foot so that the rigid component is under the ball;
   wherein, when the wearer toe walks so that the heel is off a ground, the rigid component pushes on a sensory nerve located at the ball of the foot which causes an uncomfortable sensation to the wearer, and responsive to the uncomfortable sensation, the wearer moving the heel of the foot onto the ground.

12. The method of claim 11, wherein the toe walking prevention article comprises a toe walking prevention brace, the toe walking prevention brace comprising:

the first component being a middle structure comprising the flexible material;

wherein the securing feature comprises top straps and bottom straps on respective ends of the middle structure branching off and being integrated with the middle structure, wherein the top straps and the bottom straps each having a first attachment end and oppositely located second attachment end configured to attach to the first attachment end, wherein the bottom straps are configured to wrap around the arch, and wherein the top straps are configured to wrap around at least one of the toes;

wherein the rigid component is attached to the middle structure configured for placement underneath the ball, wherein the first attachment end and the second attachment end of the top straps after the attaching are configured to hold the middle structure and the rigid component in place underneath the ball.

13. The method of claim 12, wherein the rigid component has a component length that is parallel to a length of the top straps and the bottom straps.

14. The method of claim 12, wherein the first attachment end and the second attachment end of the top straps and the bottom straps both collectively provide comprise hooks and loops, and wherein the attaching steps both comprise attaching the hooks to the loops.

15. The method of claim 12, wherein the middle structure comprises an elastomeric foam, wherein a thickness of the elastomeric foam is between 1 mm and 6 mm, and wherein an inside surface of at least the middle structure is lined with a soft fabric selected from nylon, polyester, satin, and cotton.

16. The method of claim 11, wherein the stiff material provides a Young's modulus at room temperature of at least 10 GPa.

17. The method of claim 11, wherein the toe walking prevention article comprises a toe walking prevention sock, the toe walking prevention sock comprising:

the first component being a soft material configured in an elliptical cross-sectional area, wherein the length in the length direction is configured for extending at least from an ankle of the wearer to the toes, and wherein the securing feature is provided by an elasticity of the soft material.

18. The method of claim 11, wherein the toe walking prevention article comprises a toe walking prevention sleeve, the toe walking prevention sleeve comprising:

the first component being a soft material configured in an elliptical cross-sectional area, wherein the length in the length direction is configured for extending from at least the middle of the foot but not reaching an ankle to the toes, and wherein the securing feature is provided by an elasticity of the soft material.

19. A toe walking prevention article, comprising:

a first component comprising:

a soft material or a flexible material having a length in a length direction configured for at least extending from a middle of a foot of a wearer to toes of the foot, at least one securing feature configured to be secured to the foot, wherein the securing feature comprises top straps and bottom straps on respective ends of a middle structure branching off and being integrated with the middle structure, wherein the top straps and the bottom straps each having a first attachment end and oppositely located second attachment end configured to attach to the first attachment end, wherein the bottom straps are configured to wrap around an arch of the foot, and wherein the top straps are configured to wrap around a plurality of toes; and a rigid component comprising a stiff material securely attached to the middle structure via an outer layer encasing the rigid component, configured for placement underneath a ball of the foot wherein the outer layer is permanently attached to the middle structure, wherein a surface area of the outer layer is less than a surface area of the middle structure, wherein the first component is configured for being positioned between the rigid component and the foot, and wherein the rigid component is disposed onto an outside surface of the first component, wherein the first attachment end and the second attachment end of the top straps after being attached are configured to hold the middle structure and the rigid component in place underneath the ball of the foot, and wherein the first attachment end and the second attachment end of the bottom straps after being attached are configured to hold the middle structure in place under the arch.

* * * * *